United States Patent
Oliver Garcia et al.

(10) Patent No.: US 10,624,576 B2
(45) Date of Patent: Apr. 21, 2020

(54) DEVICE FOR DIAGNOSIS AND INDUCED REGENERATION IN TISSUES BY MEANS OF THERAPEUTIC PERCUTANEOUS ELECTROLYSIS AND ELECTRO-STIMULATION TARGETED VIA BIPOLAR NEEDLE

(71) Applicant: IONCLINICS AND DEIONIC, S.L., Valencia (ES)

(72) Inventors: Josep Oliver Garcia, Valencia (ES); Vicent Allepuz Moner, Valencia (ES)

(73) Assignee: IONCLINICS AND DEIONIC, S.L., Valencia (ES)

(*) Notice: Subject to any disclaimer, the term of this patent is extended or adjusted under 35 U.S.C. 154(b) by 183 days.

(21) Appl. No.: 15/551,147

(22) PCT Filed: Feb. 3, 2016

(86) PCT No.: PCT/ES2016/070061
§ 371 (c)(1),
(2) Date: Aug. 15, 2017

(87) PCT Pub. No.: WO2016/131999
PCT Pub. Date: Aug. 25, 2016

(65) Prior Publication Data
US 2018/0028112 A1   Feb. 1, 2018

(30) Foreign Application Priority Data
Feb. 17, 2015   (ES) .................... 201500139

(51) Int. Cl.
*A61B 5/00*   (2006.01)
*A61N 1/32*   (2006.01)
(Continued)

(52) U.S. Cl.
CPC ............ *A61B 5/4836* (2013.01); *A61B 5/053* (2013.01); *A61B 5/0538* (2013.01);
(Continued)

(58) Field of Classification Search
CPC ..... A61B 5/4836; A61B 5/053; A61B 5/0538; A61B 5/6848; A61B 5/7225; A61B 5/725;
(Continued)

(56) References Cited

U.S. PATENT DOCUMENTS 7,725,193 B1   5/2010   Chu
2006/0111705 A1   5/2006   Janzen et al.
(Continued)

FOREIGN PATENT DOCUMENTS

| RU | 2161307 C1 | 12/2000 |
|----|-----------|---------|
| RU | 2229904 C2 | 1/2004 |
| SU | 1530171 A | 12/1989 |

OTHER PUBLICATIONS

International Search Report and Written Opinion dated Apr. 28, 2016 of corresponding application No. PCT/ES2016/070061; 16 pgs.
(Continued)

*Primary Examiner* — Catherine M Voorhees
*Assistant Examiner* — Roland Dinga
(74) *Attorney, Agent, or Firm* — Maier & Maier, PLLC (57) ABSTRACT

A device for use in the medical and hospital sector for the diagnosis, induced regeneration of tissue by means of therapeutic percutaneous electrolysis and targeted electro-stimulation based on the use of at least one bipolar needle that includes within a very small area of two electrodes located at the exterior and interior conductor of said bipolar needle, limiting the tissue to be treated within the bevel area of the needle without affecting the surrounding healthy tissue in
(Continued)

which said bipolar needle is applied the necessary electrical signals for diagnosing the degree of degeneration and to calculate the necessary electrical charge for treating the damaged tissue while controlling said current in a manner that eliminates the contraindications that currently exist.

2 Claims, 4 Drawing Sheets

(51) Int. Cl.
    *A61N 1/30*     (2006.01)
    *A61B 5/053*     (2006.01)
    *A61N 1/28*     (2006.01)
    *A61N 1/20*     (2006.01)
    *A61N 1/05*     (2006.01)
    *A61N 1/08*     (2006.01)
    *A61N 1/04*     (2006.01)

(52) U.S. Cl.
    CPC .......... *A61B 5/6848* (2013.01); *A61B 5/7225* (2013.01); *A61N 1/0502* (2013.01); *A61N 1/20* (2013.01); *A61N 1/28* (2013.01); *A61N 1/30* (2013.01); *A61N 1/326* (2013.01); *A61B 5/725* (2013.01); *A61N 1/0468* (2013.01); *A61N 2001/083* (2013.01)

(58) Field of Classification Search
    CPC .......... A61N 1/0502; A61N 1/20; A61N 1/28; A61N 1/30; A61N 1/326; A61N 1/0468; A61N 2001/083
    See application file for complete search history.

(56) References Cited

U.S. PATENT DOCUMENTS

2008/0027508 A1     1/2008   Chus
2012/0061257 A1     3/2012   Yu et al.
2016/0296269 A1*  10/2016  Rubinsky .................. C25B 1/26

OTHER PUBLICATIONS

Stein T. et al. "Interstitial Thermotherapy with Bipolar RF-applicators-computer aided Therapy Control and Monitoring", Proceedings of the SPIE—The International Society for Optical Engineering—1999—SPIE—USA vol. 3565, pp. 4-17, Abstract attached, 3 pgs.

* cited by examiner

DEVICE FOR DIAGNOSIS AND INDUCED REGENERATION IN TISSUES BY MEANS OF THERAPEUTIC PERCUTANEOUS ELECTROLYSIS AND ELECTRO-STIMULATION TARGETED VIA BIPOLAR NEEDLE

TECHNIQUE SECTOR

This invention is framed within the field of electro-medicine, specifically for devices destined for the diagnosis and treatment of degenerated tissues within the neuromusculoskeletal system by means of electrolysis and electro-stimulation.

INVENTION BACKGROUND

As is well known, there are electro-medical devices for achieving regeneration and recovery of neuromusculoskeletal injuries based on electrolysis and electro-stimulation.

The treatment based on percutaneous electrolysis currently uses two electrodes, anode and cathode, through which a continuous current is induced into the affected tissue which is located between these electrodes, causing heating and decomposition of the damaged tissue. The main reaction caused by the anode is the decomposition of water, leading to a reduction in the pH in its proximity while the reaction caused by the cathode gives rise to gaseous hydrogen and hydroxyl ions, thus increasing the pH in the proximity of the cathode, causing an aggression to the soft tissues affected, and a subsequent inflammation necessary for initiating the regeneration and recovery process.

The previously mentioned effects, electrolysis and tissue heating depend directly on the density of the current in circulation and the exposure time, where said current density depends on the current generated and the contact surface of the electrode. Electrical stimulation technology, as is known, is based on applying low intensity bipolar electrical impulses and this way stimulating the tissue for analgesic, anti-inflammatory, relaxing or invigorating purposes and therefore accelerating the recovery of damaged tissues.

Known within the state of the art there are electro-medical devices aimed for treating degenerated tissues of the neuromusculoskeletal system based on two electrodes that are physically separated for inducing the flow of galvanic current with the aim of initiating the regeneration of the tissues located between these electrodes, where the cathode is formed by a monopolar needle or an isolated monopolar needle, with or without a Teflon coating, which is applied to the skin in the area comprising the damaged tissue, while the anode is formed by an electrode that may be hand-held or attached to the patient's skin, as seen in the north American U.S. Pat. No. 7,725,193 of the inventor Jennifer Chu or the "Invasive Physio" device by the company Enraf Nonius. In these cases, as the electrodes are physically separated, part of the electrical current destined to treat the injured tissue where the needle is located also flows through part of the healthy tissue surrounding the damaged area, thus reducing the effectiveness of the treatment due to the low targeting of the current in the area to be treated and increasing possible side effects in healthy tissue due to the flow of current through the same. The fact that these devices require this large distance between the anode and cathode increases the bioimpedance existent between the two and leads to the need for applying greater potential difference between the electrodes to obtain the desired current. The electrical bioimpedance is greater because it affects all the tissue located between the two electrodes, both damaged tissue and healthy tissue, a problem which is resolved by the invention to which this document is dedicated.

As a consequence of the galvanic current circulating between the two electrodes along this distance, said current may affect any pathology that it may come across throughout its course, hence in these devices there are contraindications for application on patients with endoprosthesis or osteosynthesis, patients with pacemakers or any electronic implant, patients with heart problems, pregnant women, patients with malignant tumours and/or patients with thrombophiebitis.

There are well-known treatment devices and techniques that use a bipolar signal by means of two electrodes consisting in the use of superficial electrodes or monopolar needles, where depending on the lesion to the tissue to be treated and its depth, an alternating signal may be applied between the two electrodes at a specific frequency, generally of about 100 Hz. At this range of frequencies the bioimpedance of the tissue is very high, hence a very high voltage must be applied between the two electrodes, of about 100 V. These high voltages, which may further increase as the depth of the lesion increases, may affect all the tissue located between the two electrodes, regardless of whether this tissue is healthy or damaged.

On the other hand, there are other devices that use tetrapolar signals which resolve the problem described above, for which high voltages are required for obtaining the desired current due to the high bioimpedance of the tissues at the treatment frequency. These devices are based on generating between a pair of opposed electrodes an alternating current at a frequency comprised between 1.000 and 10,000 Hz. and the other pair of electrodes, positioned at 90° in relation to the previous pair of electrodes, generates the same signal with a frequency offset of about 100 Hz, which is the frequency of treatment and at the intersection of both signals in the area comprising the damaged tissue to be treated is where both signals are combined, generating a modulated signal at the frequency resulting from the frequency offset between the stimulation currents and this way, the electrical bioimpedance of the tissue is much lower and this avoids the need for applying high voltages to obtain the desired current. Even so, there remains the same problem as seen in the previous cases of the currents generated affecting all the tissue located between the electrodes, both healthy and damaged tissue, and the size of said affected tissues may be even greater the deeper the lesion. Also remains the case of not permitting its use on patients with endoprosthesis and osteosynthesis, patients with pacemakers or any electronic implant, patients with heart problems, pregnant women, patients with malignant tumours and/or patients with thrombophiebitis.

Widely known is the device of the U.S. Pat. No. 6,058,938 of the inventors Jennifer Chu and Peter Styles that uses a bipolar needle as the electrode and a superficial electrode as the return electrode for performing an electro-stimulation on the patient for the purpose of the patients experiencing less pain and discomfort during the procedure after the initial insertion of the needle, but unlike the invention referred to in this document in the case of attempting to stimulate a deep tissue part of the healthy tissue will be affected and the effectiveness of the treatment will be reduced. In addition to not having the ability to diagnose the degree of degeneration of the injured tissue for calculating the necessary current for treating said tissue.

There are patents and devices which use tissue impedance readings for location and treatment using acupuncture not presenting the ability for self-diagnosis for determining the degree of degeneration present in the examined tissue or means for adjusting the treatment signal while also deferring the use of the electrodes, and are therefore different to the invention referred to herein.

After reviewing the state of the art, there is the need for an electro-medical device that is capable of providing diagnosis and treatment by electrolysis or electro-stimulation of damaged tissues of the neuromusculoskeletal system targeted on the area comprising the damaged tissue to be treated without affecting the surrounding healthy tissue, a situation that has not been resolved in the state of the art. Consequently, the invention object of this patent allows to obtain the same treatment while reducing the electrical current required due to reducing the area of treatment, with less current applied we achieve the same density of current in the area of treatment and also obtain a more accurate and lower reading of the electrical bioimpedance value, as the electrical bioimpedance of the healthy tissue is not added, which prevents from having to apply high voltage for achieving the necessary current and also eliminates the contraindications present in the current devices for the treatment as described above.

Purpose of the Invention

The purpose of the invention consists of an electro-medical device destined to the diagnosis and treatment via percutaneous electro-stimulation of degenerated tissues of the neuromusculoskeletal system capable of targeting the treatment on the area comprising the damaged tissue without affecting the surrounding healthy tissue and consequently reducing the values of the treatment current achieving a more accurate value of the electrical bioimpedance of the damaged tissue interpreting the degree of degeneration of the same without the bioimpedance value of the healthy tissue interfering, and thus, avoiding the need for applying high voltage for generating the necessary current for its treatment, in addition to said electro-medical device eliminating the contraindications present in the current equipment such as patients with endoprosthesis and osteosynthesis, patients with pacemakers or any electronic implant, patients with heart problems, pregnant women, patients with malignant tumours and/or patients with thrombophlebitis.

DESCRIPTION OF THE INVENTION

This invention describes an electro-medical device designed for the diagnosis and treatment via percutaneous electro-stimulation of degenerated tissues within the neuroneuromusculoskeletal system.

There is an impedance difference between healthy and damaged tissues when applying alternating signals of variable frequency, as seen in the study on electrical bioimpedances on healthy tissues and tissues with tendinitis "Electrical impedance spectroscopy and diagnosis of tendinitis" by several departments of medical engineering, pathology, physical medicine and rehabilitation of South Korea, as well as the study "The dielectric properties of biological tissues" by the authors C. Gabriel. S. Gabriel and E. Corthout, of the physical medicine department of King's College. London. Hence, when assessing the degree of degeneration of the tissue, one must accurately measure the electrical bioimpedance, for which the measurement must focus solely on the affected tissue and there must always be the same distance between the two electrodes, avoiding any interference of the healthy tissue. This is why this invention is based on the use of at least one bipolar needle that comprises a very reduced area, the bevel, of two electrodes located at the exterior and interior conductor of said bipolar needle, the area of the bevel allows to focus solely on the area comprising the damaged tissue to be treated without affecting the healthy tissue.

The fact that the healthy tissue does not interfere in measuring the electrical bioimpedance, allows to obtain lower values for said bioimpedance, given that the electrical bioimpedance of the healthy tissue is not added due to not being required and thus, avoiding the need for applying high voltages for generating the necessary electrical charge for treating the tissue diagnosed as damaged.

This is why there are means for performing a self-diagnosis of the degree of degeneration of the tissue and to subsequently calculate the treatment by electrolysis, where said means are based, by means of at least one control logic in the analysis of electrical bioimpedance shown by the tissue upon applying a sinusoidal signal of variable frequency by means of at least one alternating voltage generator that comprises an oscillator which generates a clock signal towards a direct digital synthesizer (DDS) and a D/A converter for converting said digital signal into analogue; a programmable amplifier stage responsible for amplifying the signal resulting from the digital/analogue conversion and an impedance adaptor for minimising the output error of the programmable amplifier stage; an I/V converter for converting into voltage the current running through the tissue to be diagnosed. Upon applying said sinusoidal signal originating from the alternating voltage generator through a bipolar needle, this provides a more accurate action on the damaged area of the tissue, without affecting the healthy tissue surrounding the damaged area, given that said bipolar needle comprises on the same bevel two electrodes limiting the tissue to be explored in the area close-by said bevel.

Upon applying this sinusoidal signal through the bipolar needle to the tissue to be diagnosed, an electrical current goes through the tissue that is located between the two electrodes located at the bevel of the bipolar needle, where the intensity will depend on the electrical bioimpedance of the tissue that is examined. The electrical bioimpedance may vary depending on the excitation frequency, of the different types of tissue and their condition. Said induced current which runs between the two electrodes of the bipolar needle is measured allowing to calculate the complex electrical bioimpedance of the examined tissue and its dissipation factor by means of Ohm's law.

$$\text{Generator:} \quad V = V_O * sen(2\pi ft)$$

$$\text{Current:} \quad I = I_O * sen(2\pi ft + \gamma)$$

$$\text{Impedance:} \quad Z = \frac{V}{I} = \mathcal{R}_e + j\mathcal{J}_m$$

$$\text{Dissipation factor:} \quad D = \frac{\mathcal{R}_e}{\mathcal{J}_m}$$

The voltage obtained by means of the I/V converter is amplified by a programmable amplifier stage with impedance adapter and an A/D converter with low-pass filter for processing the signal. As of said processed signal, an algorithm is applied which allows to calculate the complex impedance and the dissipation factor of the diagnosed tissue where the results are stored on at least one memory device for subsequent comparison with the values obtained for a sample of healthy tissue from the same patient, control sample, or with values obtained from several clinical trials for calculating the degree of degeneration of the measured tissue and the electrical charge required for the treatment using electrolysis for stimulating the regeneration of the damaged tissue through the same bipolar needle managing to apply it only to the damaged area of the patient's tissue without affecting the healthy tissue surrounding the damaged tissue as described.

There are plans to provide means for calibrating the device so as to avoid errors when taking the bioimpedance readings by means of a multiplexer controlled from the control logic that will allow to select performing the diagnosis via the bipolar needle or performing the calibration via at least one known value calibration impedance that would allow to know the impedance error present in the device, which will be compensated during the measurement of the bioimpedance of the examined tissue.

There are means for treatment via electrolysis, selected by means of a multiplexer from the control logic, which applies the electrical charge calculated for generating the electrolysis targeted on the affected tissue without affecting the surrounding healthy tissue and avoiding the need for applying high voltages, where said means comprise at least one source of direct current that applies the calculated electrical charge to the damaged tissue via the electrodes, anode and cathode, which are located in the bevel area of a bipolar needle. The means are provided for controlling said electrical charge based on at least one ammeter that, along with the control logic, is responsible for limiting the electrical charge provided and for detecting a voltage leak controlling the current that runs through each electrode, anode and cathode, located at the bevel of said bipolar needle. This allows to compare both currents to determine whether they exceed a safety level threshold established by the control logic and for the treatment to be stopped. There is also at least one voltmeter that, along with the control logic, detects the difference in potential between the two electrodes, calculating the impedance there is between both electrodes during the treatment using electrolysis, so if the calculated impedance exceeds the maximum or minimum levels established by the control logic, the treatment will be stopped; eliminating existing contraindications in patients with endoprosthesis and osteosynthesis, patients with pacemakers or any electronic implant, patients with heart problems, pregnant women, patients with malignant tumours and/or patients with thrombophlebitis due to the improved focusing of the treatment and the control of possible current leakages.

By using the bipolar needle and the safety means mentioned above, the tissues affected by the electrical charge are limited to the area close to the bevel of the bipolar needle, completely limiting said electrical charge via the damaged tissue, without affecting the surrounding healthy tissue, avoiding the need for applying high voltages and eliminating the contraindications present in current devices.

It has means to generate the targeted electro-stimulation aimed at stimulating the sensory nerve fibres of the affected tissue which are applied from the control logic to pulsed bipolar signals through at least two bipolar needles, working these in a unipolar manner using the central conductor of each needle as an electrode and the exterior conductor as shielding.

Said pulsed signals are generated by at least one direct current generator that generates a current signal pattern formed by pulses of equal amplitude and duration, but out of synch by 180° for the average value of the signal to be null and avoid the occurrence of any phenomena of electrolysis. It also has means based on at least one ammeter and a voltmeter to control said pulsed signal based on the measurement of the current running through each electrode and on the detection of a current leakage by measuring the current that runs through each electrode located in the central conductor of each needle in a manner that allows to compare both currents to determine whether a safety level threshold established by the control logic is exceeded and stops the stimulation, and also in detecting the difference in potential between the two electrodes and thus calculate the impedance present between both electrodes during the stimulation, so if the calculated impedance exceeds certain maximum or minimum levels established by the control logic, the stimulation is stopped and this eliminates the contraindications in patients described above.

Also having foreseen the use of at least two bipolar needles and/or for at least two isolated monopolar needles, with a Teflon coating, for diagnosis, treatment and electro-stimulation.

BRIEF DESCRIPTION OF THE DRAWINGS

To complement the description provided and for the purpose of helping to better understand the characteristics of the invention, said description is accompanied by the following figures for illustrative but not limiting purposes.

DESCRIPTION OF A PREFERRED
IMPLEMENTATION MODE

Describing by way of example a preferred form of implementation of the electro-medical device destined for the treatment of degenerated tissues of the neuromusculoskeletal system, the purpose of the invention being independent from the materials used for manufacturing the device, as well as the methods of application and all accessories that may be presented, provided they do not affect its essential nature.

Figure 2:
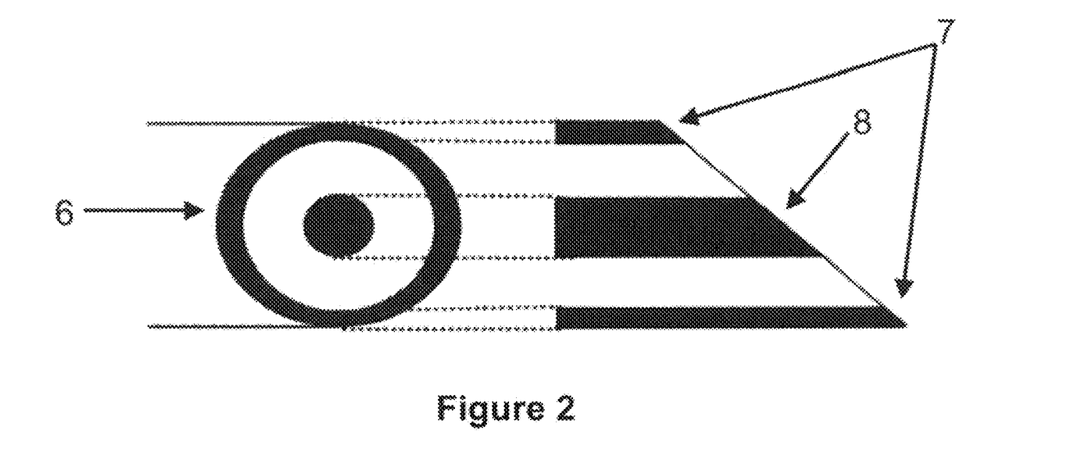
FIG. 2 is a profile view and section of a bipolar needle, indicating:
 (6) section of the bevel of a bipolar needle
 (7 and 8) Electrodes of a bipolar needle

This invention uses at least one bipolar needle that comprises in a very small area, the bevel (6), two electrodes (7 and 8) located at the exterior and interior conductor of said bipolar needle, FIG. 2, limited to the bevel area that allows to target the area comprising the damaged tissue to be treated without affecting the healthy tissue. Also the fact that the healthy tissue does not interfere in measuring the electrical bioimpedance, allows to obtain lower values for said electrical bioimpedance, given that the electrical bioimpedance of the healthy tissue is not added and thus, avoiding the need for applying high voltages for generating the necessary electrical charge for treating the damaged tissue.

Figure 1:
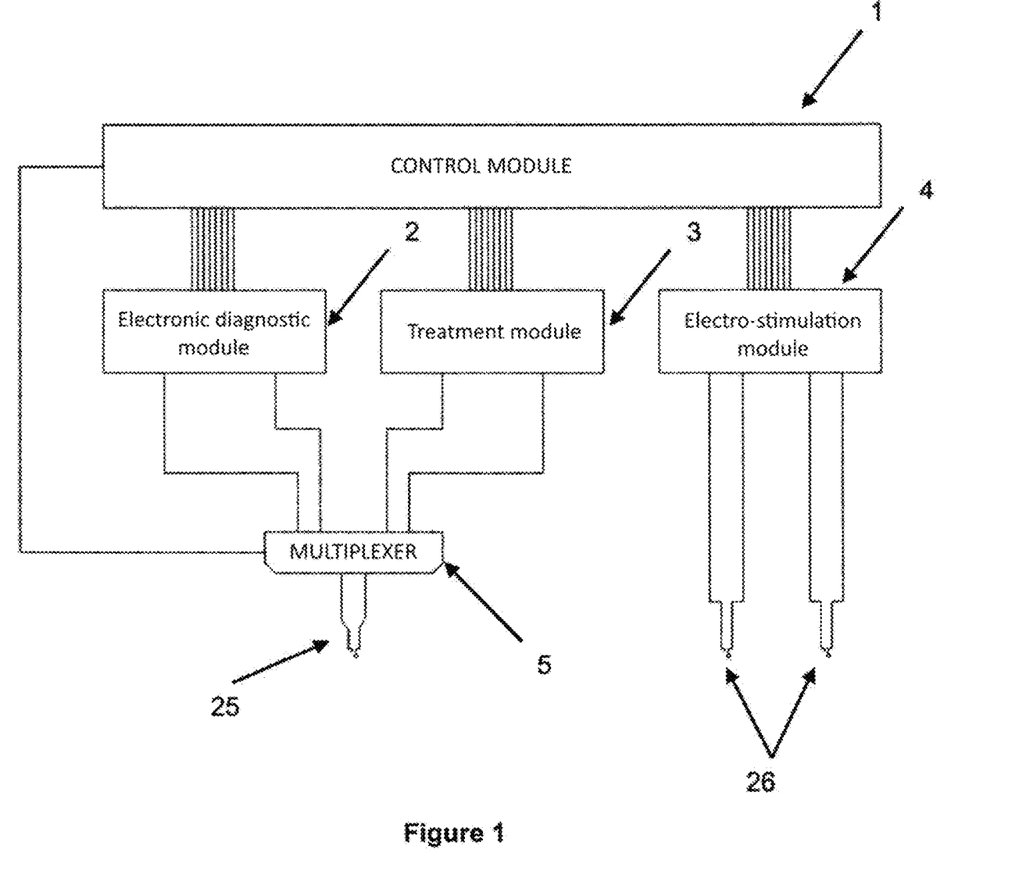
FIG. 1 is the global block diagram of the invention, displaying:
 (1) Module or control logic
 (2) Electronic diagnostic module
 (3) Treatment module
 (4) Electro-stimulation module
 (5) Multiplexer selector for diagnosis/treatment
 (25) Bipolar needle for diagnosis/treatment
 (26) Bipolar needles for targeted electro-stimulation
Figure 3:
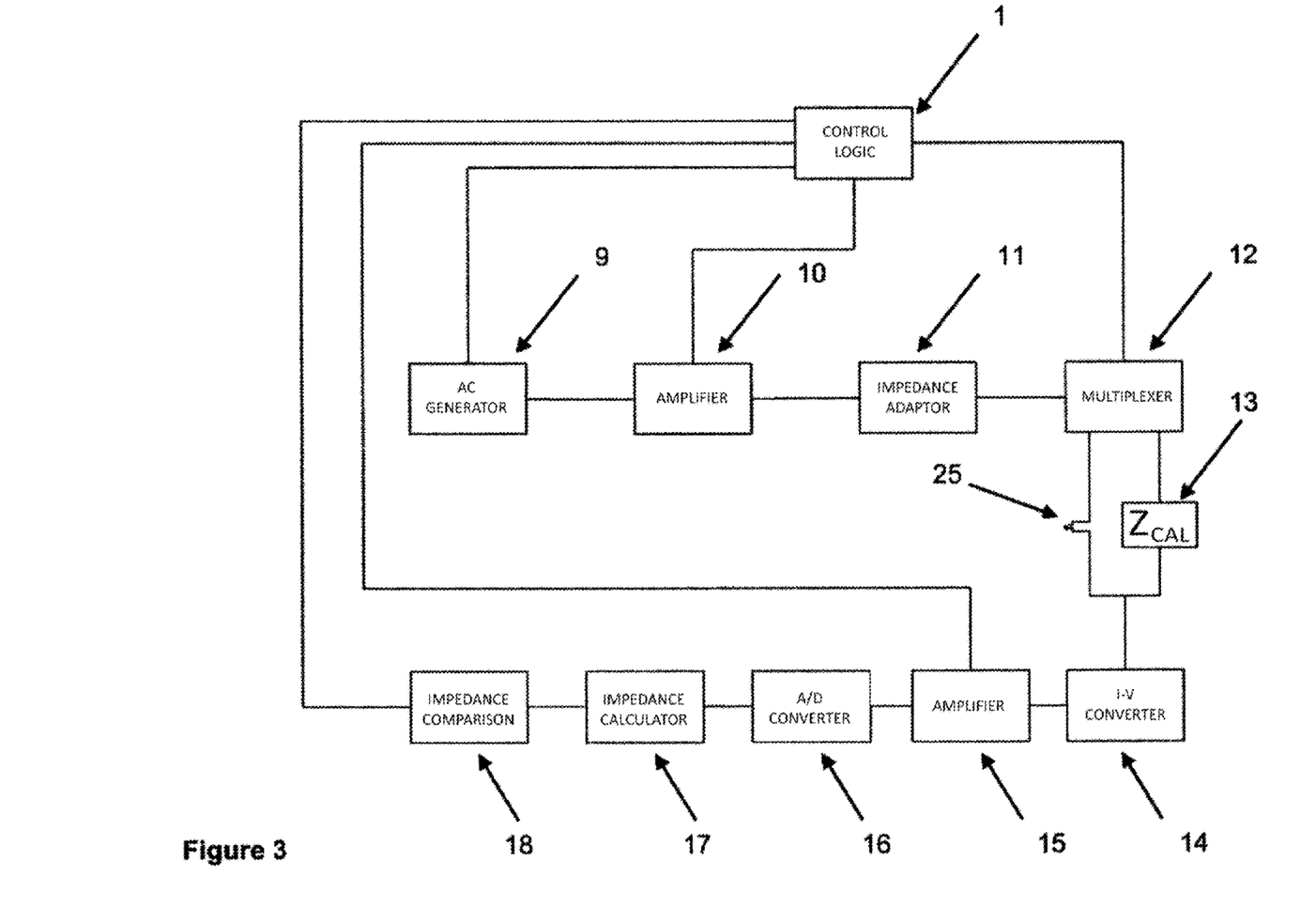
FIG. 3 represents the block diagram of the electronic diagnosis module, illustrating:
 (1) Module or control logic
 (9) Alternating voltage generator
 (10) Programmable amplifier
 (11) Impedance adapter
 (12) Multiplexer selector of bipolar needle or calibration
 (13) Known impedance for equipment calibration
 (14) I/V converter
 (15) Amplifier
 (16) A/D converter
 (17) Algorithm for estimating electrical bioimpedance
 (18) Bioimpedance comparer
 (25) Bipolar needle for diagnosis/treatment

This is why there are means for performing a self-diagnosis (2) of the degree of degeneration of the tissue and to subsequently calculate the treatment (3) by electrolysis, where said means are based, by means of at least one control logic (1) in the analysis of electrical bioimpedance shown by the tissue upon applying a sinusoidal signal of variable frequency by means of at least one alternating voltage generator (9) that comprises an oscillator that generates a clock signal towards a direct digital synthesizer (DDS) and a D/A converter for converting said digital signal into analogue; a programmable amplifier stage (10) responsible for amplifying the signal resulting from the digital/analogue conversion and an impedance adaptor (11) for minimising the output error of the programmable amplifier stage; an I/V converter (14) for converting into voltage the current running through the tissue to be diagnosed. Upon applying said sinusoidal signal from the alternating voltage generator (9) through a bipolar needle (25), this provides a more accurate action on the damaged area of the tissue, without affecting the healthy tissue surrounding the damaged area, given that said bipolar needle (25) comprises on the same bevel (6) two electrodes (7 and 8) limiting the tissue to be examined in the area close-by said bevel (6).

Upon applying said sinusoidal signal through the bipolar needle (25) to the tissue to be diagnosed, an electrical current runs through the tissue that is located between the two electrodes (7 and 8) located at the bevel (6) of the bipolar needle (25), where the intensity will depend on the electrical bioimpedance of the tissue that is examined. The electrical bioimpedance may vary depending on the excitation frequency, on the different types of tissue and their condition. Said induced current which flows between the two electrodes (7 and 8) of the bipolar needle (25) is measured allowing to calculate the complex electrical bioimpedance of the examined tissue and its dissipation factor by means of Ohm's law.

Generator: $V = V_O * sen(2\pi f t)$

Current: $I = I_O * sen(2\pi f t + \gamma)$

Impedance: $Z = \dfrac{V}{I} = \mathcal{R}_e + j\mathcal{J}_m$

Dissipation factor: $D = \dfrac{\mathcal{R}_e}{\mathcal{J}_m}$

The voltage obtained by means of the I/V converter (14) is amplified by a programmable amplifier stage (15) with impedance adapter and an A/D converter (16) with low-pass filter for processing the signal. As of said processed signal, an algorithm (17) is applied which allows to calculate the complex impedance and the dissipation factor of the diagnosed tissue where the results are stored on at least one memory device for subsequent comparison (18) with the values obtained for a sample of healthy tissue from the same patient, control sample, or with values obtained from several clinical trials for calculating the degree of degeneration of the measured tissue and the electrical charge required for determining the treatment module (3) using electrolysis for stimulating the regeneration of the damaged tissue through the same bipolar needle (25) managing to apply it only to the damaged area of the patient's tissue without affecting the healthy tissue surrounding the damaged tissue as described.

There are plans to provide means for calibrating the device to avoid errors when taking the bioimpedance readings by means of a multiplexer (5) controlled from the control logic (1) that will allow to select performing the diagnosis via the bipolar needle (25) or performing the calibration via at least one known value calibration impedance (13) that would allow to know the impedance error present in the device, which will be compensated during the measurement of the bioimpedance of the examined tissue.

Figure 4:
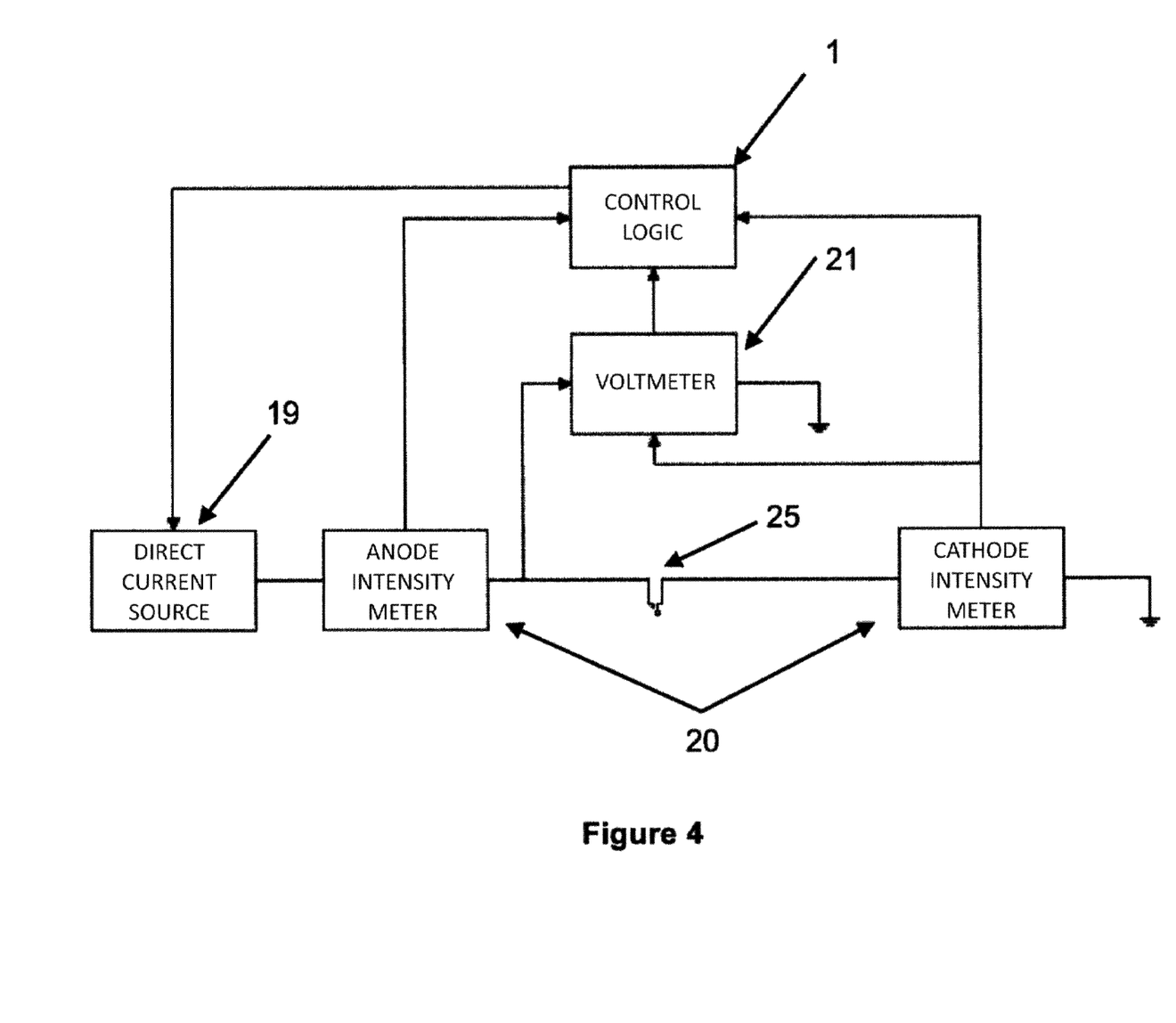
FIG. 4 illustrates the block diagram of the electrolysis treatment module, indicating:
 (1) Module or control logic
 (19) Source of direct current
 (20) Intensity meters (anode and cathode)
 (21) Voltage meter
 (25) Bipolar needle for diagnosis/treatment

There are means for treatment via electrolysis, selected by means of a multiplexer (5) from the control logic (1), which applies the electrical charge calculated for generating the electrolysis targeted on the affected tissue without affecting the surrounding healthy tissue and avoiding the need for applying high voltages, where said means comprise at least one source of direct current (19) that applies the calculated electrical charge to the damaged tissue via the electrodes (7 and 8), anode and cathode, which are located in the bevel area (6) of a bipolar needle (25). The means are provided for controlling said electrical charge based on at least one ammeter (20) that, along with the control logic (1), is responsible for limiting the electrical charge provided and for detecting a current leakage controlling the current that runs through each electrode (7 and 8), anode and cathode, located at the bevel (6) of said bipolar needle (25). This allows to compare both currents to determine whether they exceed a safety level threshold established by the control logic (1) and for the treatment (3) to be stopped. There is also at least one voltmeter (21) that, along with the control logic (1), detects the difference in potential between the two electrodes (7 and 8), calculating the impedance there is between both electrodes during the treatment, so if the calculated impedance exceeds the maximum or minimum levels established by the control logic (1) the treatment (3) will be stopped, eliminating existing contraindications in patients with endoprosthesis and osteosynthesis, patients with pacemakers or any electronic implant, patients with heart problems, pregnant women, patients with malignant tumours and/or patients with thrombophlebitis due to the improved focusing of the treatment and the control of possible current leakages.

Due to using the bipolar needle (25) and the safety means mentioned above, the tissues affected by the electrical charge are limited to the area close to the bevel (6) of the bipolar needle (25), completely limiting said electrical charge via the damaged tissue, without affecting the surrounding healthy tissue, avoiding the need for applying high voltages and eliminating the contraindications present in current devices.

Figure 5:
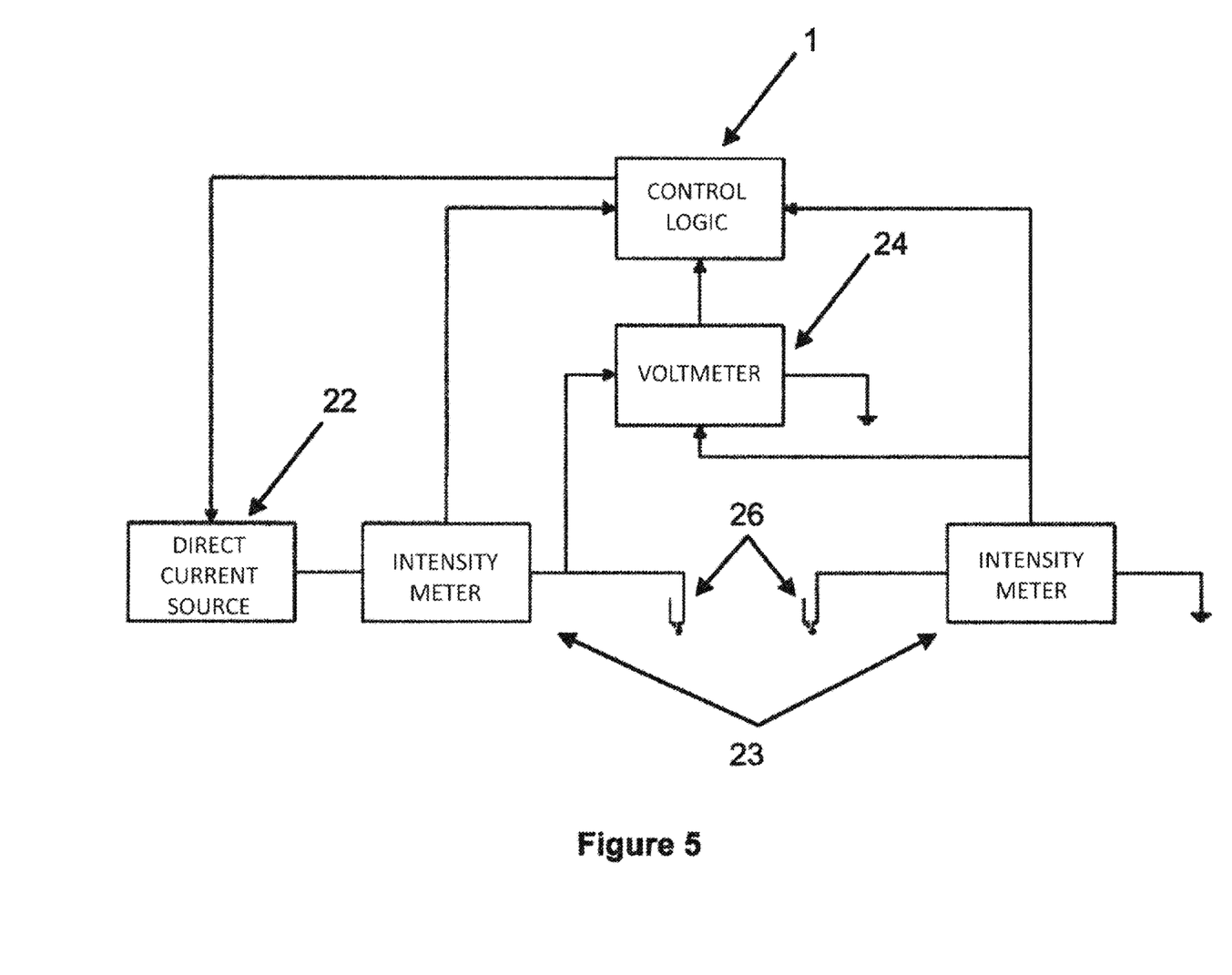
FIG. 5 represents the block diagram of the electro-stimulation module, illustrating:
 (1) Module or control logic
 (22) Source of direct current
 (23) Intensity meters
 (24) Voltage meter
 (26) Bipolar needles for electro-stimulation

It has means to generate the targeted electro-stimulation (4) aimed at stimulating the sensory nerve fibres of the affected tissue which are applied from the control logic (1) to pulsed bipolar signals through at least two bipolar needles (26), working these in a unipolar manner using the central conductor of each needle as an electrode and the exterior conductor as shielding.

Said pulsed signals are generated by at least one direct current generator (22) that generates a current signal pattern formed by pulses of equal amplitude and duration, but out of synch by 180° for the average value of the signal to be null and avoid the occurrence of any phenomena of electrolysis. It also has means based on at least one ammeter (23) and a voltmeter (24) which, along with the control logic (1), controls said pulsed signal based on the measurement of the current running through each electrode and on the detection of a current leakage by measuring the current that runs through each electrode located in the central conductor of each needle in a manner that allows to compare both currents to determine whether a safety level threshold established by the control logic (1) is exceeded and stops the electro-stimulation (4), and also in detecting the difference in potential between the two electrodes and thus calculate the impedance present between both electrodes during the stimulation, so if the calculated impedance exceeds certain maximum or minimum levels established by the control logic, the electro-stimulation (4) is stopped and this eliminates the contraindications in patients described above.

Also having foreseen the use of at least two bipolar needles and/or for at least two isolated monopolar needles, with a Teflon coating, for diagnosis, treatment and electro-stimulation.

The invention claimed is:

1. A device for diagnosis and induced regeneration of tissues using therapeutic percutaneous electrolysis and electro-stimulation targeted through a bipolar needle, and configured to allow self-diagnosis targeted on the area of damaged tissue to be treated without affecting the surrounding healthy tissue, the device comprising:
    at least one AC voltage generator that comprises an oscillator configured to generate a clock signal for a direct digital synthesizer (DDS),
    a control logic configured to apply a sinusoidal signal through the at least one AC voltage generator;
    a D/A converter which performs a digital/analogue conversion on the sinusoidal signal received from the AC voltage generator;
    a programmable amplifier configured to amplify the signal resulting from the digital/analogue conversion;
    an impedance adaptor configured to minimize an output error of the programmable amplifier;
    an I-V converter configured to convert the current that runs through the tissue into voltage, wherein said voltage is amplified by the programmable amplifier with the impedance adaptor,
    an A/D converter with low-pass filter for processing the signal measured from the voltage amplified by the I-V converter;
    a direct current generator and a memory, said memory configured to be processed by the control logic for generating a dosage of electric charge of the bipolar needle by the at least one direct current generator;
    a module for generating the targeted electro-stimulation, comprising at least one direct current converter, at least one ammeter and at least two bipolar needles, each bipolar needle comprising a central conductor and an exterior conductor, wherein the direct current converter is configured to generate a bipolar pulse signal that is applied to the tissue by the at least two bipolar needles, whereby the central conductor of each needle acts as an electrode and its exterior conductor acts as shielding, and the module is adapted for detecting current leakages that run through each electrode based on the at least one ammeter along with the control logic, and wherein the module is also adapted for detecting a potential difference between two electrodes and an impedance between the two electrodes by at least one voltmeter along with the control logic, wherein the control logic limits a maximum and a minimum value that stop the treatment.

2. The device of claim 1, further comprising a Teflon coating on at least one bipolar needle and at least two isolated monopolar needles.

* * * * *